(12) United States Patent  
Asaba

(10) Patent No.: US 8,735,848 B2  
(45) Date of Patent: May 27, 2014

(54) CHARGED PARTICLE BEAM TREATMENT PLANNING DEVICE AND CHARGED PARTICLE BEAM TREATMENT PLANNING METHOD

(71) Applicant: Sumitomo Heavy Industries, Ltd., Tokyo (JP)

(72) Inventor: Toru Asaba, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/939,921

(22) Filed: Jul. 11, 2013

(65) Prior Publication Data

US 2014/0018603 A1   Jan. 16, 2014

(30) Foreign Application Priority Data

Jul. 13, 2012   (JP) .................... 2012-157876

(51) Int. Cl.
*A61N 5/10*   (2006.01)
*A61N 5/00*   (2006.01)
*H01J 3/14*   (2006.01)

(52) U.S. Cl.
USPC ............ 250/396 R; 250/492.3; 250/503.1

(58) Field of Classification Search
USPC ........... 250/396 R, 396 ML, 398, 400, 482.1, 250/484.5, 492.1, 492.2, 492.21, 492.22, 250/492.23, 492.3, 503.1
See application file for complete search history.

(56) References Cited

U.S. PATENT DOCUMENTS

| | | | | |
|---|---|---|---|---|
| 6,777,700 | B2* | 8/2004 | Yanagisawa et al. | 250/492.3 |
| 8,049,187 | B2* | 11/2011 | Tachikawa | 250/492.1 |
| 8,153,989 | B2* | 4/2012 | Tachikawa et al. | 250/396 R |
| 2002/0005494 | A1* | 1/2002 | Kamijo et al. | 250/491.1 |
| 2009/0242789 | A1* | 10/2009 | Tachikawa | 250/396 R |
| 2010/0072389 | A1* | 3/2010 | Tachikawa et al. | 250/396 R |
| 2011/0240874 | A1* | 10/2011 | Iwata | 250/396 ML |
| 2012/0119105 | A1* | 5/2012 | Iwata | 250/396 ML |
| 2012/0264998 | A1* | 10/2012 | Fujitaka et al. | 600/1 |
| 2014/0014851 | A1* | 1/2014 | Asaba | 250/396 R |

FOREIGN PATENT DOCUMENTS

JP   2009-236867 A   10/2009

* cited by examiner

*Primary Examiner* — Bernard E Souw
(74) *Attorney, Agent, or Firm* — Rader, Fishman & Grauer PLLC

(57) ABSTRACT

There is provided a charged particle beam treatment planning device that creates a treatment plan and is connected to a charged particle beam irradiation apparatus that includes a scanning electromagnet, which scans a charged particle beam, and a degrader, which adjusts a range of the charged particle beam by reducing the energy of the charged particle beam, and irradiates an irradiation object with the charged particle beam. The charged particle beam treatment planning device includes a control unit that adjusts the dose of the charged particle beam, which is irradiated to a predetermined position of the irradiation object, on the basis of a passing distance of the charged particle beam within the degrader calculated using a deflection angle of the charged particle beam.

7 Claims, 15 Drawing Sheets

US 8,735,848 B2

CHARGED PARTICLE BEAM TREATMENT PLANNING DEVICE AND CHARGED PARTICLE BEAM TREATMENT PLANNING METHOD

INCORPORATION BY REFERENCE

Priority is claimed to Japanese Patent Application No. 2012-157876, filed Jul. 13, 2012, the entire content of each of which is incorporated herein by reference.

BACKGROUND

1. Technical Field

The present invention relates to a charged particle beam treatment planning device and a charged particle beam treatment planning method for creating a treatment plan for irradiating an irradiation object with a charged particle beam using a charged particle beam irradiation apparatus.

2. Description of the Related Art

A charged particle beam treatment planning device is known that creates a treatment plan for irradiating an irradiation object with a charged particle beam using a charged particle beam irradiation apparatus disclosed in the related art. The charged particle beam irradiation apparatus disclosed in the related art is an apparatus for performing treatment by irradiating a tumor within the body of a patient with a charged particle beam. The charged particle beam irradiation apparatus includes a cyclotron that generates a charged particle beam by accelerating a charged particle, a scanning electromagnet that scans the charged particle beam, and a degrader that is provided on a downstream side of the scanning electromagnet in an irradiation direction of the charged particle beam and adjusts the range of the charged particle beam by reducing the energy of the charged particle beam. The degrader is a plate-like member that extends with a fixed thickness in a scanning direction perpendicular to the irradiation direction of the charged particle beam.

A charged particle beam treatment planning device in the related art creates a treatment plan regarding how to control the charged particle beam irradiation apparatus by calculating the dose distribution of the charged particle beam irradiated to the irradiation object. The charged particle beam irradiation apparatus irradiates the irradiation object with the charged particle beam on the basis of the treatment plan created by the charged particle beam treatment planning device.

SUMMARY

According to an embodiment of the present invention, there is provided a charged particle beam treatment planning device that creates a treatment plan and is connected to a charged particle beam irradiation apparatus that includes a scanning electromagnet, which scans a charged particle beam, and a degrader, which adjusts a range of the charged particle beam by reducing energy of the charged particle beam, and irradiates an irradiation object with the charged particle beam. The charged particle beam treatment planning device includes a control unit that adjusts a dose of the charged particle beam, which is irradiated to a predetermined position of the irradiation object, on the basis of a passing distance of the charged particle beam within the degrader calculated using a deflection angle of the charged particle beam.

DETAILED DESCRIPTION

However, there has been a difference between the dose distribution calculated by the charged particle beam treatment planning device and the dose distribution of the charged particle beam, which is actually irradiated to the charged particle beam irradiation apparatus, in some cases. Therefore, it has been required to improve the accuracy of the treatment plan.

It is desirable to provide a charged particle beam treatment planning device and a charged particle beam treatment planning method capable of creating an accurate treatment plan.

Figure 5:
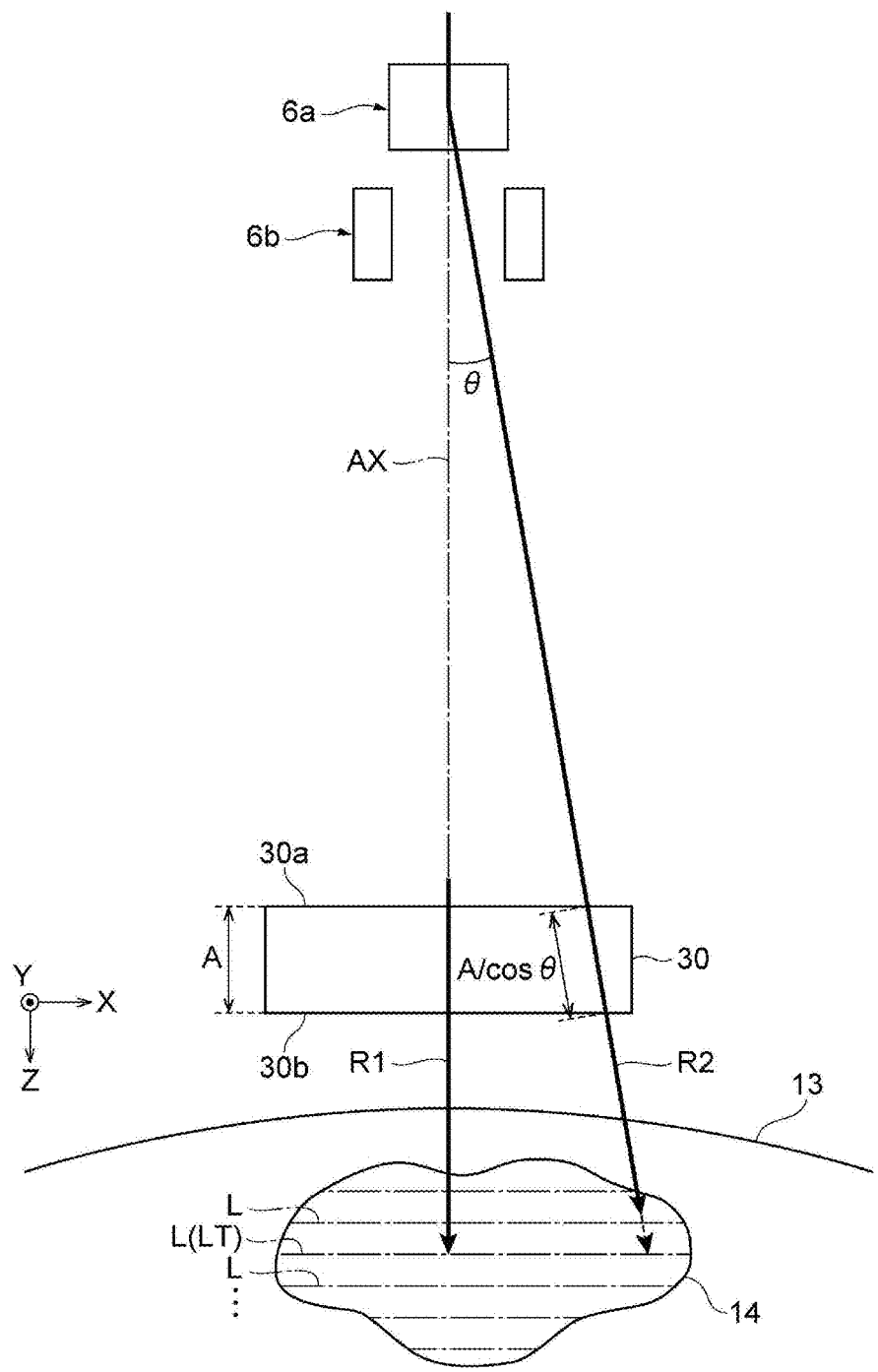
FIG. 5 is a schematic diagram showing the relationship between the deflection angle of a charged particle beam and the passing distance of the charged particle beam within a degrader.

For example, as shown in FIG. 5, when a degrader having a rectangular cross-section in the irradiation direction of the charged particle beam is used, a charged particle beam made to go straight without being deflected by the scanning electromagnet is perpendicularly incident on the degrader. Accordingly, the passing distance of the charged particle beam within the degrader is equal to the thickness of the degrader. On the other hand, in the case of a charged particle beam deflected by the scanning electromagnet, the passing distance of the charged particle beam within the degrader is increased if the deflection angle is large. In this case, since the energy of the charged particle beam decreases as the passing distance of the charged particle beam within the degrader increases, the range of the charged particle beam becomes short. For this reason, when creating a treatment plan without considering the changes in the range due to the deflection angle of the charged particle beam, there may be a slight difference between the dose of the charged particle beam for a predetermined position of the irradiation object, which is calculated by the charged particle beam treatment planning device, and the actual value. However, the charged particle beam treatment planning device according to the embodiment of the present invention includes a control unit that adjusts the dose of the charged particle beam, which is irradiated to the predetermined position of the irradiation object, on the basis of the passing distance of the charged particle beam within the degrader. Therefore, even if the passing distance of the charged particle beam within the degrader changes with the deflection angle of the charged particle beam, it is possible to suppress the occurrence of a difference between the treatment plan and the actual irradiation since the control unit can adjust the dose in consideration of the passing distance. As a result, it is possible to create a high-accuracy treatment plan.

In addition, in the charged particle beam treatment planning device according to the embodiment of the present invention, it is preferable that the control unit include a dose distribution calculation section that calculates a dose distribution of the charged particle beam irradiated to the irradiation object and the dose distribution calculation section calculate the dose distribution of the charged particle beam irradiated to the irradiation object by adding the dose of the charged particle beam irradiated to the predetermined position to a dose of the charged particle beam, which is irradiated to another position of the irradiation object on a more upstream side than the predetermined position in the irradiation direction of the charged particle beam, on the basis of the passing distance of the charged particle beam within the degrader. In this case, even if the range becomes short due to an increase in the passing distance of the charged particle beam within the degrader and accordingly the actual charged particle beam is irradiated to the more upstream side than the predetermined position, the dose distribution calculation section can calculate the dose distribution by adding the dose of the charged particle beam irradiated to the predetermined position to the dose of the charged particle beam, which is irradiated to another position on the upstream side, in consideration of such a dose of the charged particle beam. Therefore, since it is possible to suppress the occurrence of a difference between the dose distribution calculated in the treatment planning and the actual dose distribution, it is possible to create a high-accuracy treatment plan.

In addition, in the charged particle beam treatment planning device according to the embodiment of the present invention, it is preferable that the control unit include a layer setting section that virtually divides the irradiation object into a plurality of layers along an irradiation direction of the charged particle beam and the layer setting section set a distance between the layers to β. Preferably, when an amount of decrease in the range of the charged particle beam due to a change of the passing distance when irradiating the charged particle beam to the predetermined position after deflecting the charged particle beam in one layer with respect to the passing distance when irradiating the charged particle beam without deflecting the charged particle beam in the one layer is greater than β/2, the dose distribution calculation section calculates the dose distribution of the charged particle beam irradiated to the irradiation object by adding the dose of the charged particle beam irradiated to the predetermined position to another dose of the charged particle beam irradiated to another position in another layer located on an upstream side of the one layer. The dose distribution calculation section improves the accuracy by adding the dose of the charged particle beam irradiated to the predetermined position to the dose of the charged particle beam irradiated to another position when the amount of decrease in the range is large, while the dose distribution calculation section determines that there is little influence and does not perform the addition when the amount of decrease in the range is small. In this manner, it is possible to reduce the load of the operation while improving the accuracy of a treatment plan.

In addition, according to another embodiment of the present invention, there is provided a charged particle beam treatment planning device that creates a treatment plan and is connected to a charged particle beam irradiation apparatus including an irradiation nozzle, in which a scanning electromagnet that scans a charged particle beam and a degrader that is provided on a downstream side of the scanning electromagnet and adjusts a range of the charged particle beam by reducing energy of the charged particle beam are housed. The charged particle beam treatment planning device includes: a storage unit that stores a CT image of the irradiation object; a layer setting section that virtually divides the irradiation object into a plurality of layers along an irradiation direction of the charged particle beam on the basis of the CT image stored in the storage unit; an irradiation position setting unit that sets an irradiation position of the charged particle beam in each of the plurality of layers; and a dose distribution calculation unit that, on the basis of a passing distance of the charged particle beam within the degrader when irradiating the charged particle beam to a predetermined irradiation position in a predetermined layer of the plurality of layers, calculates a dose distribution of the charged particle beam irradiated to the irradiation object by adding a dose of the charged particle beam irradiated to the predetermined irradiation position to a dose of the charged particle beam irradiated to an irradiation position in a layer located on a more upstream side in the irradiation object than the predetermined irradiation position in the irradiation direction of the charged particle beam.

In this charged particle beam treatment planning device, even if the range becomes short due to an increase in the passing distance of the charged particle beam within the degrader and accordingly the actual charged particle beam is irradiated to the more upstream side than the predetermined irradiation position in a predetermined layer, the dose distribution calculation section can calculate the dose distribution by adding the dose of the charged particle beam irradiated to the predetermined irradiation position to the dose of the charged particle beam in the layer on the upstream side in consideration of such a dose of the charged particle beam. As a result, since it is possible to suppress the occurrence of a difference between the dose distribution calculated in the treatment planning and the actual dose distribution, it is possible to create a high-accuracy treatment plan.

In addition, according to still another embodiment of the present invention, there is provided a charged particle beam treatment planning method for creating a treatment plan for charged particle beam treatment. The charged particle beam treatment planning method includes: calculating a passing distance of a charged particle beam within a degrader, which adjusts a range of the charged particle beam, using a deflection angle of the charged particle beam; and adjusting a dose of the charged particle beam irradiated to a predetermined position of an irradiation object on the basis of the calculated passing distance.

When creating a treatment plan without considering the changes in the range due to the deflection angle of the charged particle beam, there may be a slight difference between the dose of the charged particle beam for a predetermined position of the irradiation object, which is calculated in the treatment planning, and the actual value. However, in the charged particle beam treatment planning method according to the embodiment of the present invention, the dose of the charged particle beam irradiated to the predetermined position of the irradiation object is adjusted on the basis of the passing distance of the charged particle beam within the degrader. Therefore, even if the passing distance of the charged particle beam within the degrader changes with the deflection angle of the charged particle beam, it is possible to suppress the occurrence of a difference between the treatment plan and the actual irradiation since it is possible to adjust the dose in consideration of the passing distance. As a result, it is possible to create a high-accuracy treatment plan.

In addition, in the charged particle beam treatment planning method according to the embodiment of the present invention, it is preferable to further include calculating a dose distribution of the charged particle beam irradiated to the irradiation object by adding the dose of the charged particle beam irradiated to the predetermined position to a dose of the charged particle beam, which is irradiated to another position of the irradiation object on a more upstream side than the predetermined position in the irradiation direction of the charged particle beam, on the basis of the calculated passing distance. In this case, even if the range becomes short due to an increase in the passing distance of the charged particle beam within the degrader and accordingly the actual charged particle beam is irradiated to the more upstream side than the predetermined position, it is possible to calculate the dose distribution by adding the dose of the charged particle beam irradiated to the predetermined position to the dose of the charged particle beam, which is irradiated to another position on the upstream side, in consideration of such a dose of the charged particle beam. Therefore, since it is possible to suppress the occurrence of a difference between the dose distribution calculated in the treatment planning and the actual dose distribution, it is possible to create a high-accuracy treatment plan.

In addition, in the charged particle beam treatment planning method according to the embodiment of the present invention, it is preferable to further include: virtually dividing the irradiation object into a plurality of layers along an irradiation direction of the charged particle beam every distance $\beta$; and when an amount of decrease in a range of the charged particle beam due to a change of the passing distance when irradiating the charged particle beam to the predetermined position after deflecting the charged particle beam in one layer with respect to the passing distance when irradiating the charged particle beam without deflecting the charged particle beam in the one layer is greater than $\beta/2$, calculating the dose distribution of the charged particle beam irradiated to the irradiation object by adding the dose of the charged particle beam irradiated to the predetermined position to a dose of the charged particle beam irradiated to another position in another layer located on an upstream side of the one layer. When the amount of decrease in the range is large, the accuracy is improved by adding the dose of the charged particle beam irradiated to the predetermined position to the dose of the charged particle beam irradiated to another position. On the other hand, when the amount of decrease in the range is small, it is determined that there is little influence and the addition is not performed. In this manner, it is possible to reduce the load of the operation while improving the accuracy of a treatment plan.

Hereinafter, preferred embodiments of the present invention will be described in detail with reference to the accompanying drawings. In addition, in the following explanation, the same or corresponding components are denoted by the same reference numerals and repeated explanation thereof will be omitted.

Figure 1:
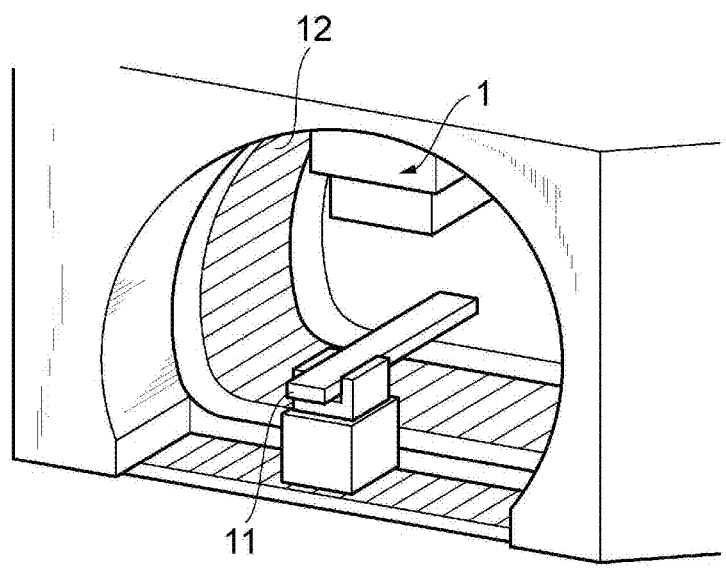
FIG. 1 is a perspective view of a charged particle beam irradiation apparatus that performs treatment on the basis of a treatment plan created by a charged particle beam treatment planning device according to an embodiment of the present invention.

FIG. 1 is a perspective view of a charged particle beam irradiation apparatus that performs treatment on the basis of a treatment plan created by a charged particle beam treatment planning device according to an embodiment of the present invention. As shown in FIG. 1, a charged particle beam irradiation apparatus 1 is fixed to a rotating gantry 12 that is provided so as to surround a treatment table 11. The charged particle beam irradiation apparatus 1 is rotatable around the treatment table 11 by the rotating gantry 12. In addition, the charged particle beam irradiation apparatus 1 is a charged particle beam treatment apparatus for treating a tumor.

Figure 2:
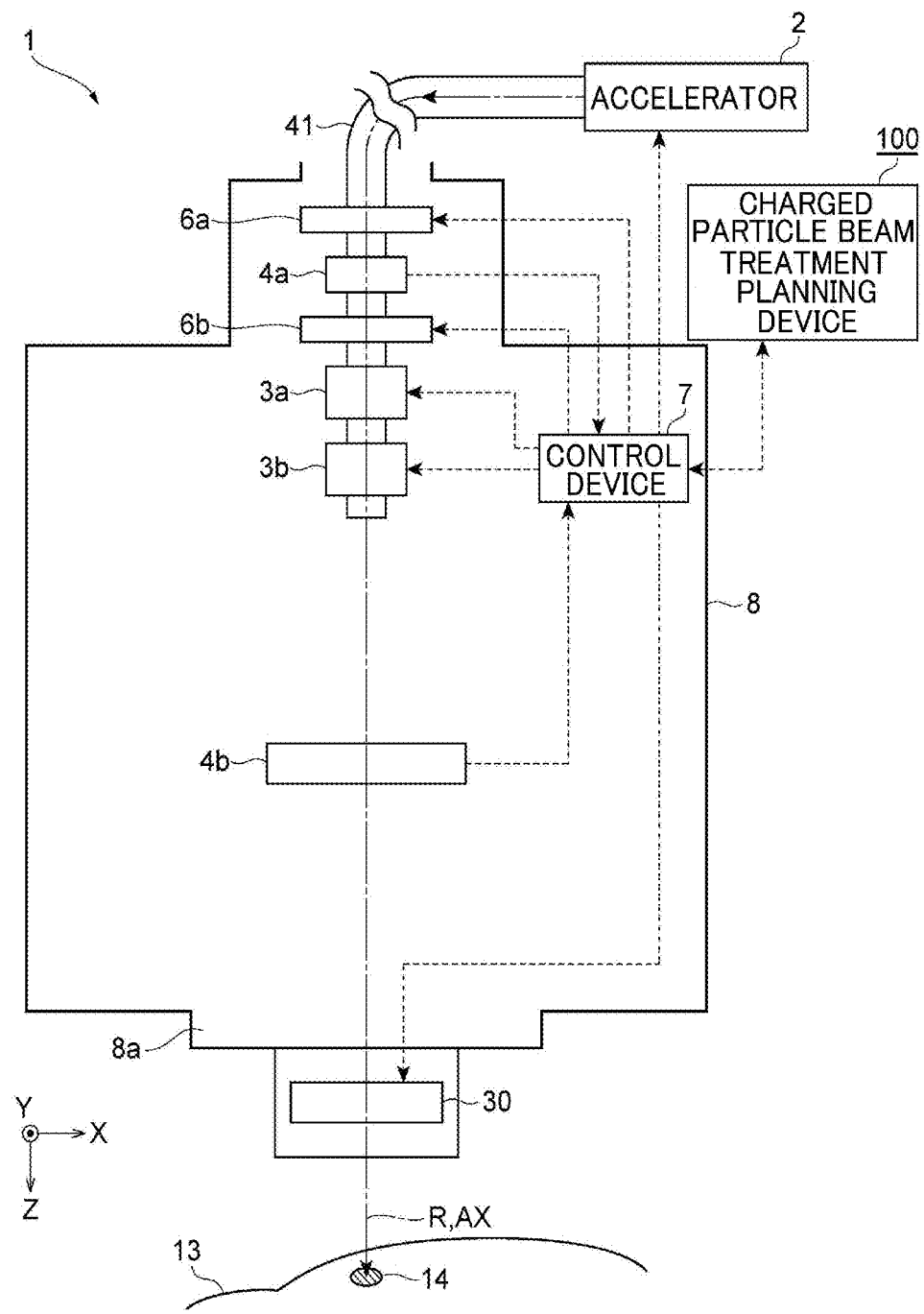
FIG. 2 is a schematic diagram showing the configuration of a charged particle beam treatment planning device and a charged particle beam irradiation apparatus that irradiates a charged particle beam using a scanning method.
Figure 3:
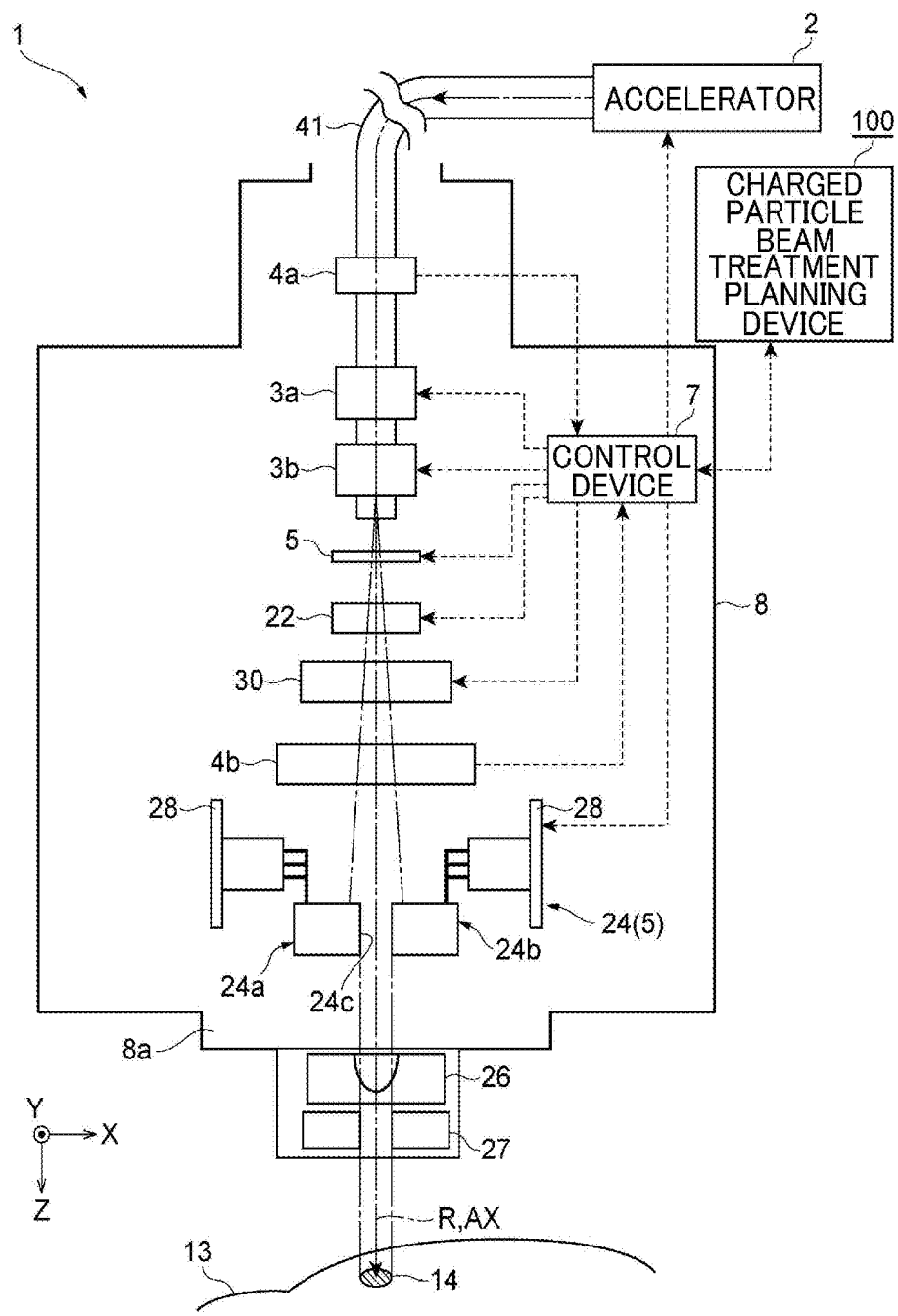
FIG. 3 is a schematic diagram showing the configuration of a charged particle beam treatment planning device and a charged particle beam irradiation apparatus that irradiates a charged particle beam using a wobbler method.

FIG. 2 is a schematic diagram showing the configuration of a charged particle beam treatment planning device and a charged particle beam irradiation apparatus that irradiates a charged particle beam using a scanning method. FIG. 3 is a schematic diagram showing the configuration of a charged particle beam treatment planning device and a charged particle beam irradiation apparatus that irradiates a charged particle beam using a wobbler method. As shown in FIGS. 2 and 3, the charged particle beam irradiation apparatus 1 irradiates a tumor (irradiation object) 14 within the body of a patient 13 with a charged particle beam R. The charged particle beam R is obtained by accelerating a changed particle at high speed. For example, a proton beam, a heavy particle (heavy ion) beam, and the like can be mentioned. In addition, the wobbler method is also referred to as a broad beam method. The charged particle beam irradiation apparatus 1 and a charged particle beam treatment planning device 100 are connected to each other through a network cable or the like so that data transmission and reception therebetween are possible.

In addition, the following explanation will be given using terms of "X direction", "Y direction", and "Z direction". The "Z direction" is a direction in which the base axis AX of the charged particle beam R extends. In addition, the "base axis AX" is assumed to be an irradiation axis of the charged particle beam R when the charged particle beam R is not deflected by scanning electromagnets 3a and 3b to be described later. FIGS. 2 and 3 show that the charged particle beam R is irradiated along the base axis AX. In addition, in the following explanation, a direction in which the charged particle beam R is irradiated along the base axis AX is assumed to be the "irradiation direction of charged particle beam R". The "X direction" is one direction within the plane perpendicular to the Z direction. The "Y direction" is a direction perpendicular to the X direction within the plane perpendicular to the Z direction.

First, the configuration of the charged particle beam irradiation apparatus that performs treatment using the treatment plan created by the charged particle beam treatment planning device according to the present embodiment will be described with reference to FIG. 2. The configuration of the charged particle beam irradiation apparatus according to the scanning method will be described. As shown in FIG. 2, the charged particle beam irradiation apparatus 1 includes an accelerator 2, scanning electromagnets 3a and 3b, monitors 4a and 4b, convergence bodies 6a and 6b, a degrader 30, and a control device 7. The scanning electromagnets 3a and 3b, the monitors 4a and 4b, the convergence bodies 6a and 6b, the degrader 30, and the control device 7 are housed in an irradiation nozzle 8. However, the control device 7 may be provided outside the irradiation nozzle 8. The charged particle beam treatment planning device 100 is connected to the control device 7. When the charged particle beam irradiation apparatus 1 performs treatment, the charged particle beam treatment planning device 100 creates a treatment plan in advance and transmits the treatment plan to the control device 7 of the charged particle beam irradiation apparatus 1. The control device 7 irradiates the charged particle beam R on the basis of the received treatment plan.

The accelerator 2 is a source that generates the charged particle beam R continuously by accelerating charged particles. As examples of the accelerator 2, a cyclotron, a synchrotron, a cyclo-synchrotron, and a linac can be mentioned. The charged particle beam R generated in the accelerator 2 is transferred to the irradiation nozzle 8 by the beam transfer system. The accelerator 2 is connected to the control device 7, and the current or the like of the charged particle beam R supplied from the accelerator 2 is controlled by the control device 7.

The scanning electromagnets 3a and 3b are formed by a pair of electromagnets. By changing the magnetic field between a pair of electromagnets according to the signal supplied from the control device 7, the charged particle beam R passing between the electromagnets is scanned. The X-direction scanning electromagnet 3a scans the charged particle beam R in the X direction (first scanning direction), and the Y-direction scanning electromagnet 3b scans the charged particle beam R in the Y direction (second scanning direction perpendicular to the first scanning direction). These scanning electromagnets 3a and 3b are disposed in this order on the downstream side of the accelerator 2 on the base axis AX. In addition, the scanning electromagnets 3a and 3b may also be disposed in order of the scanning electromagnets 3b and 3a without being limited to the arrangement based on the above order.

The monitor 4a monitors (detects) the beam position of the charged particle beam R, and the monitor 4b monitors (detects) the absolute value of the dose of the charged particle beam R and the dose distribution of the charged particle beam R. Each of the monitors 4a and 4b outputs the monitoring information (detection value) to the control device 7. The monitor 4a is disposed on the downstream side of the accelerator 2 and on the upstream side of the X-direction scanning electromagnet 3a on the base axis AX of the charged particle beam R. The monitor 4b is disposed on the downstream side of the Y-direction scanning electromagnet 3b on the base axis AX.

The convergence bodies 6a and 6b narrow the charged particle beam R so as to converge, for example. Electromagnets are used as convergence bodies 6a and 6b herein. The convergence body 6a is disposed between the accelerator 2 and the monitor 4a on the base axis AX, and the convergence body 6b is disposed between the monitor 4a and the scanning electromagnet 3a on the base axis AX.

The degrader 30 adjusts the range of the charged particle beam R by reducing the energy of the charged particle beam R passing therethrough. In addition, in the adjustment of the range, rough adjustment is performed by a degrader (not shown) provided immediately after the accelerator 2, and fine adjustment is performed by the degrader 30 in the irradiation nozzle 8. The degrader 30 is located on the base axis AX, is provided on a downstream side of the scanning electromagnets 3a and 3b in the irradiation direction of the charged particle beam R and adjusts the maximum arrival depth of the charged particle beam R within the body of the patient 13. The degrader 30 is a plate-like member extending in the X and Y directions. In addition, in the present embodiment, the "range" is a movement distance of the charged particle beam R until the charged particle beam R loses kinetic energy and stops. More specifically, assuming that the maximum dose is 100%, the range is a depth, at which the dose is 90%, on a deeper side than the irradiation distance (depth) when the maximum dose is obtained. When irradiating the tumor 14 with the charged particle beam R, the tumor 14 is virtually divided into a plurality of layers L in a Z direction (for example, refer to FIG. 5), and irradiation is performed in an irradiation range set in each layer L while scanning the charged particle beam R along a predetermined scanning pattern. After the irradiation of the charged particle beam R with respect to one layer L is completed, the degrader 30 (in addition, a degrader provided immediately after the accelerator 2 may also used) adjusts the range, and irradiation of the charged particle beam R with respect to another layer L is performed. The degrader 30 is disposed at a position of about 1500 mm to 2000 mm from the Y-direction scanning electromagnet 3b.

The range of the charged particle beam R is adjusted by changing the passing distance of the charged particle beam R within the degrader 30. For example, it is possible to adjust the range by replacing the degrader 30 itself disposed on the irradiation axis of the charged particle beam R with a degrader having a different thickness. Alternatively, it is also possible to adjust the range by changing the number of degraders 30 disposed on the base axis AX of the charged particle beam R in a configuration where a plurality of degraders 30 can be disposed in the Z direction. In this case, the arrangement and removal of the degrader 30 onto and from the base axis AX of the charged particle beam R are possible by providing an actuator, which can reciprocate in the plane perpendicular to the Z direction, for each degrader 30 and controlling the actuator.

A position where the degrader 30 is provided is not particularly limited as long as it is a more downstream side than the scanning electromagnets 3a and 3b. However, when the scanning method is adopted, it is preferable to provide the degrader 30 on the more downstream side than the monitor 4b. In the present embodiment, the degrader 30 is provided at a distal end 8a of the irradiation nozzle 8. In addition, the distal end of the irradiation nozzle 8 is an end on the downstream side in the irradiation direction of the charged particle beam R.

The control device 7 is configured to include a CPU, a ROM, and a RAM, for example. The control device 7 controls the accelerator 2, the scanning electromagnets 3a and 3b, and the convergence bodies 6a and 6b on the basis of the monitoring information output from the monitors 4a and 4b.

When irradiating the charged particle beam R in the scanning method using the charged particle beam irradiation apparatus 1 shown in FIG. 2, the degrader 30 that can perform adjustment to the predetermined range is set, and the convergence bodies 6a and 6b are changed to the operating state (ON) so that the charged particle beam R passing therethrough converges.

Then, the charged particle beam R is emitted from the accelerator 2. The emitted charged particle beam R is scanned by controlling the scanning electromagnets 3a and 3b, and the range of the charged particle beam R is adjusted by the degrader 30. In this manner, the charged particle beam R is irradiated while being scanned within the irradiation range in one layer L set in the Z direction for the tumor 14. After the irradiation to one layer L is completed, the charged particle beam R is irradiated to the next layer L.

The configuration of a charged particle beam irradiation apparatus according to the wobbler method will be described with respect to FIG. 3. As shown in FIG. 3, the charged particle beam irradiation apparatus 1 includes the accelerator 2, the scanning electromagnets 3a and 3b, the monitors 4a and 4b, a scatterer 5, a ridge filter 22, a multi-leaf collimator 24, a bolus 26, a patient collimator 27, the degrader 30, and the control device 7. The scanning electromagnets 3a and 3b, the monitors 4a and 4b, the scatterer 5, the ridge filter 22, the multi-leaf collimator 24, the bolus 26, the patient collimator 27, degrader 30, and the control device 7 are housed in the irradiation nozzle 8. However, the control device 7 may be provided outside the irradiation nozzle 8. In addition, the same portions as in the charged particle beam irradiation apparatus 1 shown in FIG. 2 will be omitted.

The scatterer 5 diffuses the charged particle beam R passing therethrough into a wide beam having a spread in a direction perpendicular to the irradiation axis. The scatterer 5 has a plate shape, and is formed of tungsten having a thickness of several millimeters, for example. The scatterer 5 is disposed on the downstream side of the scanning electromagnet 3b and the upstream side of the monitor 4b on the base axis AX.

The ridge filter 22 adjusts the dose distribution of the charged particle beam R. Specifically, the ridge filter 22 gives a spread-out Bragg peak (SOBP) to the charged particle beam R so as to correspond to the thickness (length in the irradiation direction) of the tumor 14 within the body of the patient 13. The ridge filter 22 is disposed on the downstream side of the scatterer 5 and the upstream side of the monitor 4b on the base axis AX.

The degrader 30 is disposed between the ridge filter 22 and the monitor 4b on the base axis AX. The degrader 30 has the same function and configuration as those described in FIG. 2, and can adjust the range using the same method. The degrader 30 is disposed at a position of about 1000 mm to 1800 mm from the scatterer 5.

The multi-leaf collimator (hereinafter, referred to as an "MLC") 24 serves to shape the shape (planar shape) of the charged particle beam R in a plane direction perpendicular to the irradiation direction, and has light shielding portions 24a and 24b including a plurality of comb teeth. The light shielding portions 24a and 24b are disposed so as to face each other, and an opening 24c is formed between the light shielding portion 24a and 24b. The MLC 24 cuts out the charged particle beam R having a contour corresponding to the shape of the opening 24c by allowing the charged particle beam R to pass through the opening 24c.

In addition, the MLC 24 can change the position and shape of the opening 24c by moving the light shielding portion 24a and 24b back and forth in a direction perpendicular to the Z direction. In addition, the MLC 24 is guided along the irradiation direction by a linear guide 28, and is movable along the Z direction. The MLC 24 is disposed on the downstream side of the monitor 4b.

The bolus 26 shapes the three-dimensional shape of a portion of the maximum arrival depth of the charged particle beam R according to the shape of a maximum depth portion of the tumor 14. The shape of the bolus 26 is calculated on the basis of the outline of the tumor 14 and the electron density of surrounding tissue calculated from the data of X-ray CT, for example. The bolus 26 is disposed on the downstream side of the MLC 24 on the base axis AX. The patient collimator 27 finally shapes the planar shape of the charged particle beam R according to the planar shape of the tumor 14. The patient collimator 27 is disposed on the downstream side of the bolus 26 on the base axis AX. The patient collimator 27 may be used instead of the MLC 24, or both the MLC 24 and the patient collimator 27 may be used. The bolus 26 and the patient collimator 27 are provided at the distal end 8a of the irradiation nozzle 8.

When irradiating the charged particle beam R in the wobbler method using the charged particle beam irradiation apparatus 1 shown in FIG. 3, the degrader 30 that can perform adjustment to the predetermined range is set, and the light shielding portion 24a and 24b of the MLC 24 are moved back and forth so that the opening 24c has a predetermined shape.

Then, the charged particle beam R is emitted from the accelerator 2. The emitted charged particle beam R is scanned so as to draw a circle by the scanning electromagnets 3a and 3b and is diffused by the scatterer 5, and is then shaped and adjusted by the ridge filter 22, the degrader 30, the MLC 24, the bolus 26, and the patient collimator 27. As a result, the charged particle beam R is irradiated to the tumor 14 so as to have a uniform irradiation range along the shape of the tumor 14.

In addition, it is also possible to adopt a configuration to perform both the scanning method and the wobbler method using the same charged particle beam irradiation apparatus 1. That is, it is possible to provide the components shown in FIG. 2 and the components shown in FIG. 3, and remove the components used only in the wobbler method when the scanning method is adopted and remove the components used only in the scanning method when the wobbler method is adopted.

Figure 4:
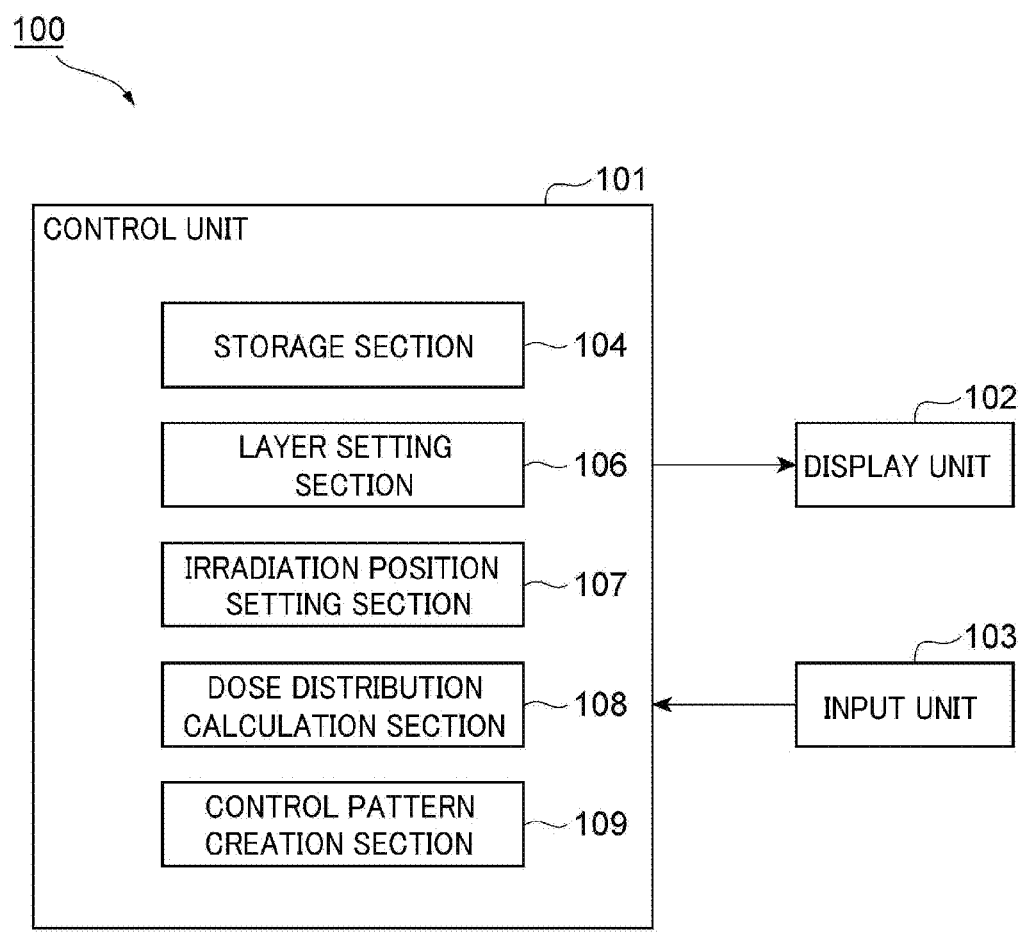
FIG. 4 is a block diagram showing the configuration of the charged particle beam treatment planning device according to the embodiment of the present invention.

Next, the configuration of the charged particle beam treatment planning device 100 will be described with reference to FIG. 4. FIG. 4 is a block diagram showing the configuration of the charged particle beam treatment planning device 100 according to the present embodiment. The charged particle beam treatment planning device 100 is an apparatus that creates a treatment plan for irradiating the tumor 14 with the charged particle beam R using the above-described charged particle beam irradiation apparatus 1. The charged particle beam treatment planning device 100 includes a control unit 101, a display unit 102, and an input unit 103. The display unit 102 has a function of displaying the information required for creating a treatment plan for the user, and is configured to include a display device or the like. The input unit 103 has a function of inputting the required information by the user's operation in order to create a treatment plan, and is configured to include a mouse, a touch panel, a pen tablet, a keyboard, or the like. In addition, when the control unit 101 performs a process for creating a treatment plan fully automatically, it is possible to omit the display unit 102 and the input unit 103.

The control unit 101 is configured to include a CPU, a ROM, and a RAM, for example. The control unit 101 has a function of performing control processing for creating a treatment plan using the charged particle beam treatment planning device 100. In the present embodiment, the control unit 101 has a function of adjusting the dose of the charged particle beam R, which is irradiated to a predetermined position of the tumor 14, on the basis of the passing distance of the charged particle beam R within the degrader 30.

The control unit 101 reduces a difference between the actual dose of the charged particle beam R irradiated to the predetermined position of the tumor 14 and the dose calculated in the treatment planning by adjusting the dose of the charged particle beam R irradiated to the predetermined position of the tumor 14 on the basis of the passing distance of the charged particle beam R within the degrader 30, thereby creating a high-accuracy treatment plan. Specifically, the control unit 101 includes a storage section 104, a layer setting section 106, an irradiation position setting section 107, a dose distribution calculation section 108, and a control pattern creation section 109.

The storage section 104 has a function of acquiring and storing various kinds of information used for treatment planning. The storage section 104 can output the stored information at a required timing. The storage section 104 has a function of acquiring a CT image of the tumor 14 from at least a CT image creation apparatus (not shown) and storing the CT image.

The layer setting section 106 has a function of virtually dividing the tumor 14 into a plurality of layers L along the irradiation direction of the charged particle beam R (irradiation direction of the charged particle beam R irradiated along the base axis AX). The layer setting section 106 sets a distance between layers when virtually dividing the tumor 14 and divides the tumor 14 into the plurality of layers L at distances of about 2 to 10 mm, for example.

The irradiation position setting section 107 has a function of setting a position, to which the charged particle beam R is irradiated, in each layer L. The irradiation position setting section 107 has a function of setting an irradiation range (Region of Interest: ROI) of the charged particle beam R for each of the plurality of layers L and setting a scanning pattern of the charged particle beam R so that the ROI is covered.

The dose distribution calculation section 108 has a function of calculating the dose distribution of the charged particle beam R irradiated to the tumor 14. The dose distribution calculation section 108 calculates the dose distribution of the charged particle beam R irradiated to the tumor 14 by adding the dose of the charged particle beam R, which is irradiated to a predetermined irradiation position of each layer L, to the dose of the charged particle beam irradiated to an irradiation position of another layer L, which is located on the more upstream side in the tumor 14 than the layer L in the irradiation direction of the charged particle beam R, on the basis of the passing distance of the charged particle beam R within the degrader 30. In addition, when the amount of decrease in the range of the charged particle beam R due to the change of the passing distance of the charged particle beam R within the degrader 30 when irradiating the charged particle beam R to a predetermined irradiation position after deflecting the charged particle beam R in the predetermined layer L with respect to the passing distance of the charged particle beam R within the degrader 30 when irradiating the charged particle beam R without deflecting the charged particle beam R in the predetermined layer L is greater than $\beta/2$ (where $\beta$ is a distance between the layers L, the dose distribution calculation section 108 calculates the dose distribution of the charged particle beam R irradiated to the tumor 14 by adding the dose of the charged particle beam R, which is irradiated to the irradiation position of the predetermined layer L, to the dose of the charged particle beam R irradiated to the irradiation position of another layer L on the upstream side. In addition, the dose distribution calculation section 108 has a function of comparing the calculated dose distribution with that in the ROI, evaluating the calculated dose distribution, and performing determination of OK or NG.

The control pattern creation section 109 has a function of creating the control pattern of the scanning electromagnets 3a and 3b so that the charged particle beam R is irradiated to the tumor 14 according to the determined scanning pattern.

Figure 6:
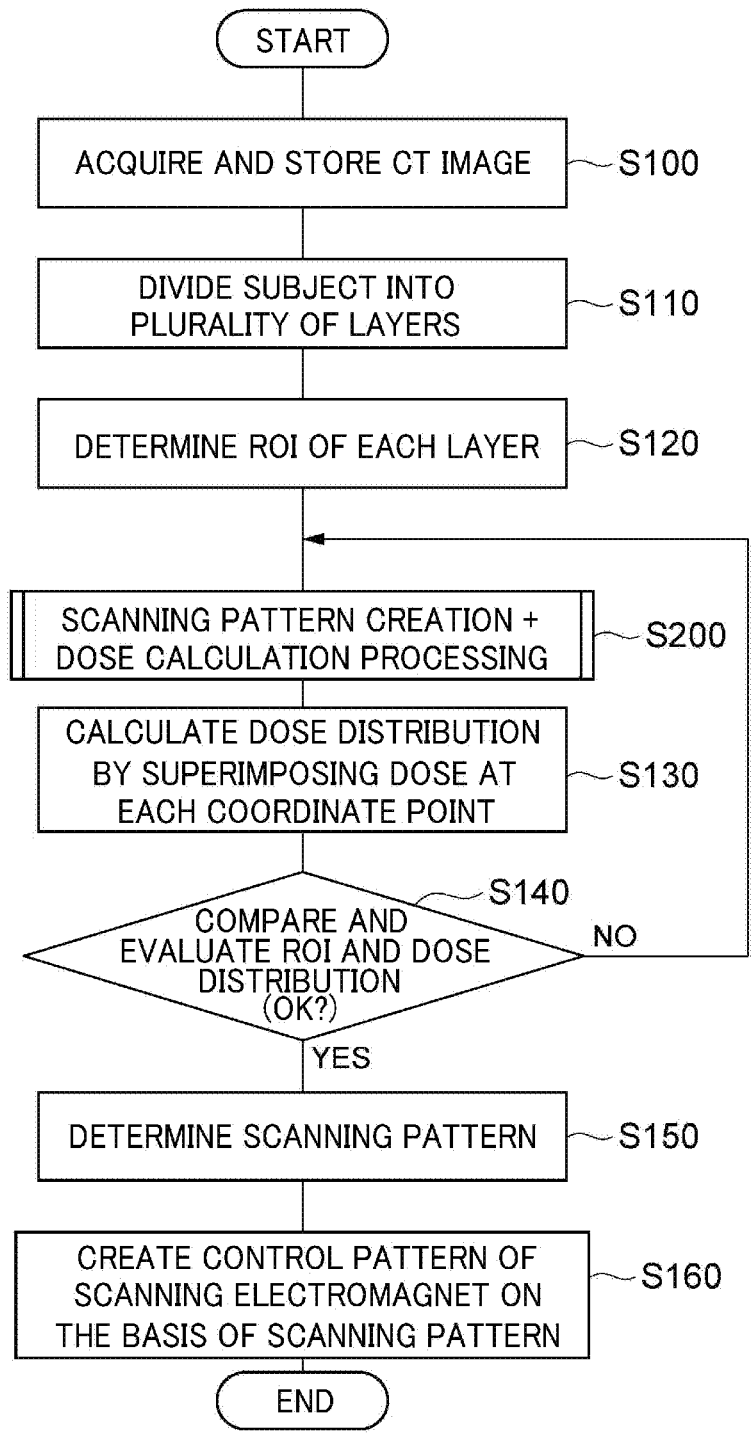
FIG. 6 is a flow chart showing the process of creating a treatment plan of the charged particle beam treatment planning device according to the embodiment of the present invention.
Figure 7:
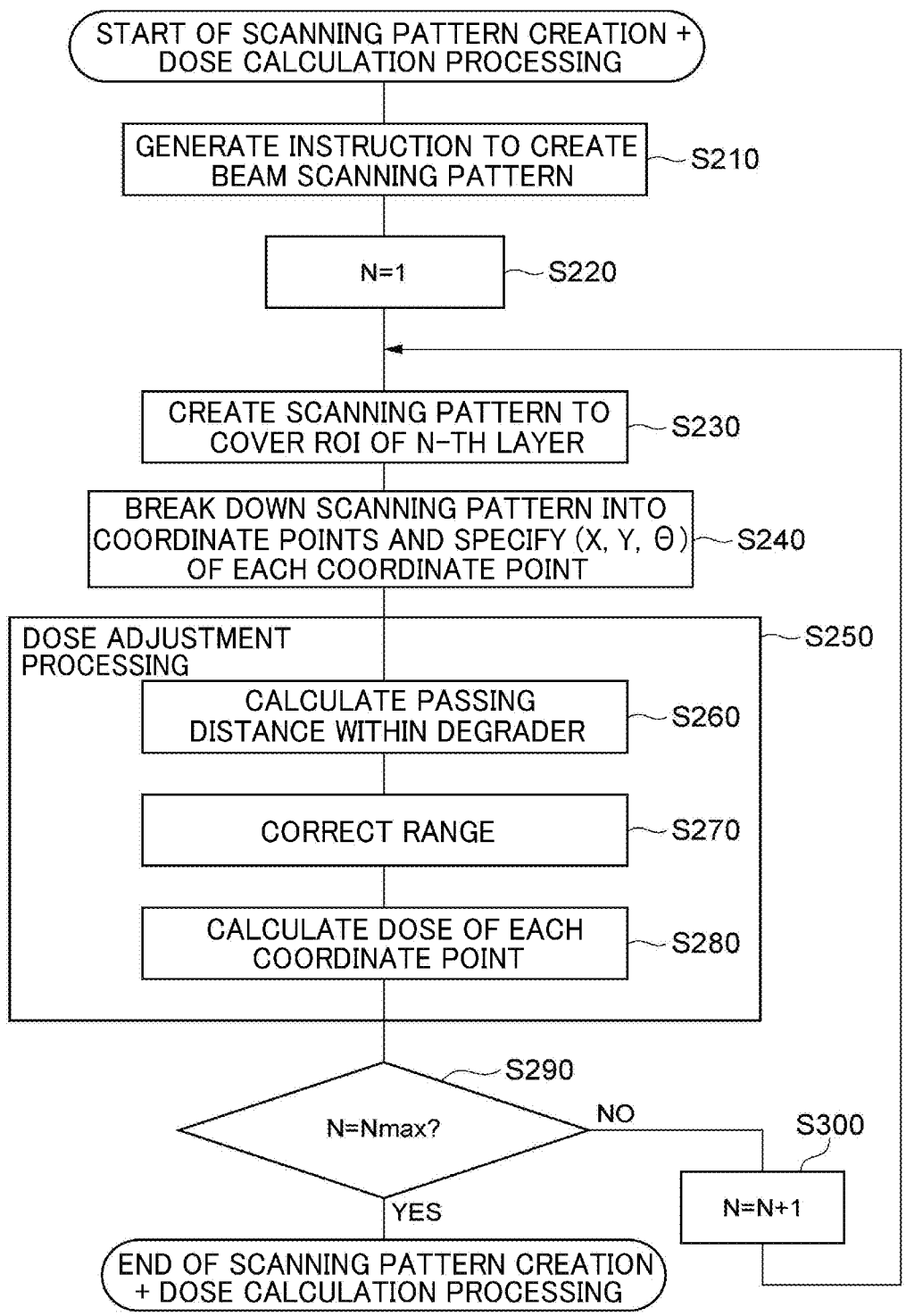
FIG. 7 is a flow chart showing the process of creating a treatment plan of the charged particle beam treatment planning device according to the embodiment of the present invention.

Next, a process when the charged particle beam treatment planning device 100 creates a treatment plan will be described with reference to FIGS. 6 and 7. FIGS. 6 and 7 are flow charts showing the process when the charged particle beam treatment planning device 100 according to the present embodiment creates a treatment plan. The process shown in FIGS. 6 and 7 is performed at a predetermined timing by the control unit 101 of the charged particle beam treatment planning device 100 before performing treatment using the charged particle beam irradiation apparatus 1 after a CT image creation apparatus (not shown) ends the creation of a CT image around the tumor 14 of the patient 13. In addition, an example of creating a treatment plan when performing treatment using a scanning method will be described. In addition, the process shown below is just an example, and may the order of steps or the content of each step in the process may be appropriately changed.

Figure 8:
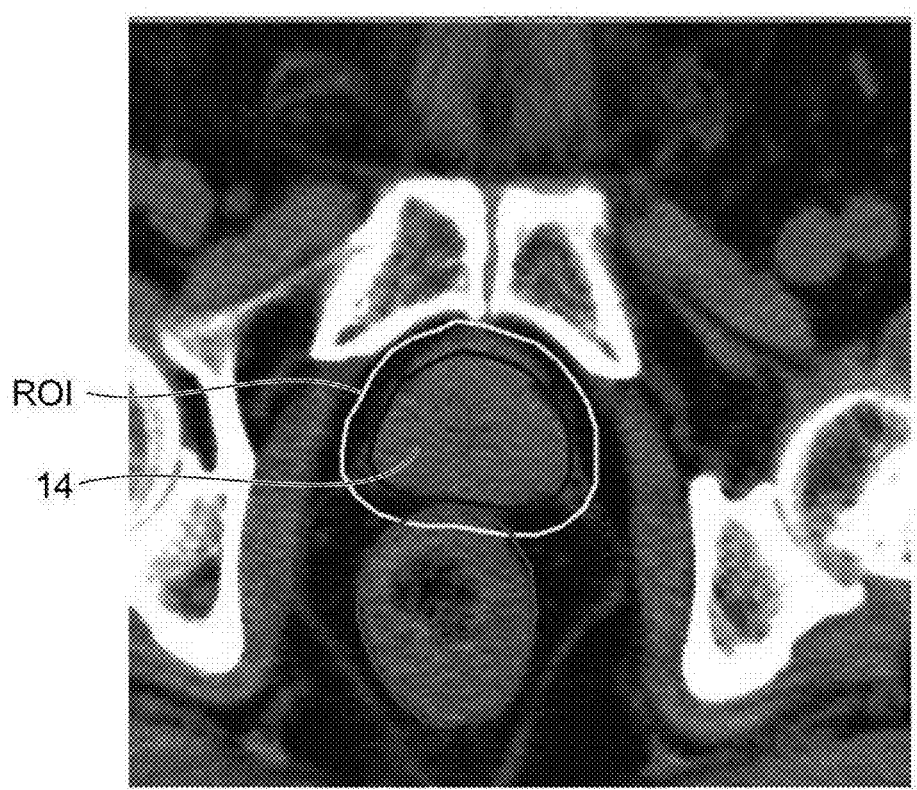
FIG. 8 is a diagram showing an example of an image of a predetermined layer.

As shown in FIG. 6, the control unit 101 acquires a CT image around the tumor 14 from a CT image creation apparatus (not shown) and stores the acquired CT image in the storage section 104 (step S100). Here, the control unit 101 creates a three-dimensional image of the tumor 14 on the basis of the CT image stored in the storage section 104. In addition, the control unit 101 sets an irradiation direction of the charged particle beam R irradiated to the tumor 14 (irradiation direction of the charged particle beam R irradiated along the base axis AX). Then, the layer setting section 106 virtually divides the tumor 14 into a plurality of layers L along the Z direction, which is the irradiation direction of the charged particle beam R, on the basis of the CT image stored in the storage section 104 (step S110). The layer setting section 106 virtually divides the tumor 14 into the plurality of layers L perpendicular to the set irradiation direction at predetermined distances. In addition, the layer setting section 106 acquires a cross-sectional image of a three-dimensional image of the tumor 14 at a position corresponding to each layer L. For example, an image shown in FIG. 8 is acquired.

Then, the irradiation position setting section 107 determines an irradiation range (Region of Interest: ROI) of the charged particle beam R, that is, a range where treatment is to be performed for each layer L set in S110 (step S120). Determination of the ROI is performed on the basis of the image of each layer L. For example, it is possible to specify the position of the tumor 14 from the image of the layer L shown in FIG. 8 and determine a portion (portion surrounded by the white line in FIG. 8), which surrounds the tumor 14, as an ROI. In addition, the irradiation position setting section 107 may determine the ROI by performing an operation based on the image of each layer L, or may determine the ROI on the basis of a user's input. When the ROI is determined on the basis of a user's input, the control unit 101 outputs the image of each layer L to the display unit 102. The user examines which portion of the image is to be irradiated with the charged particle beam R with reference to the image of each layer L displayed on the display unit 102, and specifies an ROI in the image by operating the input unit 103. The irradiation position setting section 107 determines the ROI in each layer L by acquiring the user input information.

Then, the control unit 101 creates a scanning pattern of the charged particle beam R for the ROI in each layer L and performs a dose calculation process (step S200). As shown in FIG. 7, when an instruction to create a scanning pattern of the charged particle beam R is given (step S210), the process shown in FIG. 7 is started. The instruction to create a scanning pattern may be automatically generated at a predetermined timing by the control unit 101, or may be generated by the user's operation of the input unit 103.

Figure 9:
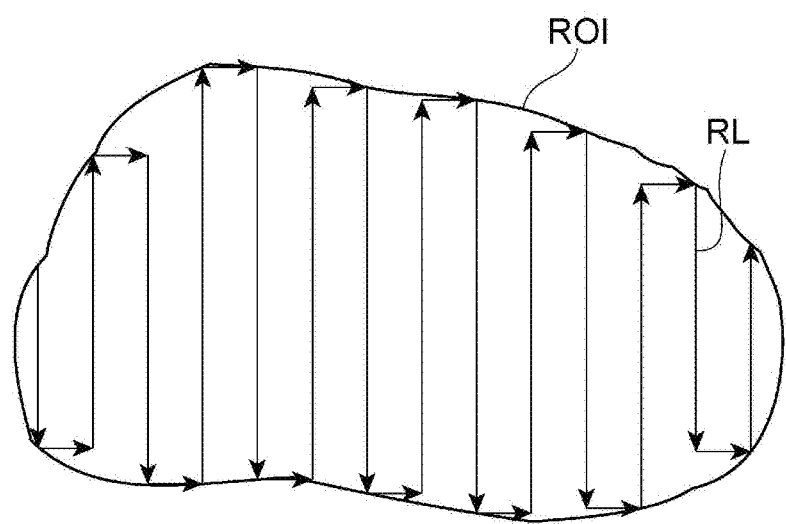
FIG. 9 is a diagram showing an example of the scanning pattern of the charged particle beam set to cover the ROI of a predetermined layer.

Then, for each layer L, a scanning pattern is created, and the dose of the charged particle beam R irradiated to the predetermined position of the tumor 14 is calculated while being adjusted on the basis of the passing distance of the charged particle beam R within the degrader 30 (steps S220 to S300). First, the control unit 101 sets the number N of the layer L to 1 in order to perform an operation in order from the layer L on the downstream side (step S220). The irradiation position setting section 107 creates a scanning pattern of the charged particle beam R for the layer L so that the ROI of the N-th (N=1) layer L from the downstream side is covered (step S230). In addition, the scanning speed may be set to a fixed speed. FIG. 9 shows an example of the scanning pattern. The irradiation position setting section 107 creates a scanning pattern by drawing a scanning path RL for the ROI. In addition, the irradiation position setting section 107 may create a scanning pattern automatically by performing an operation based on the image of each layer L, or may create a scanning pattern on the basis of a user's input. When a scanning pattern is created on the basis of a user's input, the control unit 101 outputs the image of each layer L to the display unit 102. The user examines how to draw the scanning path RL for the ROI shown in the image with reference to the image of each layer L displayed on the display unit 102, and specifies a scanning pattern by operating the input unit 103. The irradiation position setting section 107 determines the scanning pattern in each layer L by acquiring the user input information. In addition, although a continuous scan of the charged particle beam R is performed in the example shown in FIG. 9, it is also possible to create a scanning pattern by performing a spot scan to irradiate the charged particle beam R intermittently (in a spot shape).

Then, in order to calculate the dose distribution of the ROI, the dose distribution calculation section 108 decomposes the scanning pattern set in S230 into coordinate points and specifies (X, Y, θ) of each coordinate point (step S240). In addition, θ is a deflection angle of the irradiation axis of the charged particle beam R, which is irradiated to the coordinate point, with reference to the base axis AX.

Figure 10:
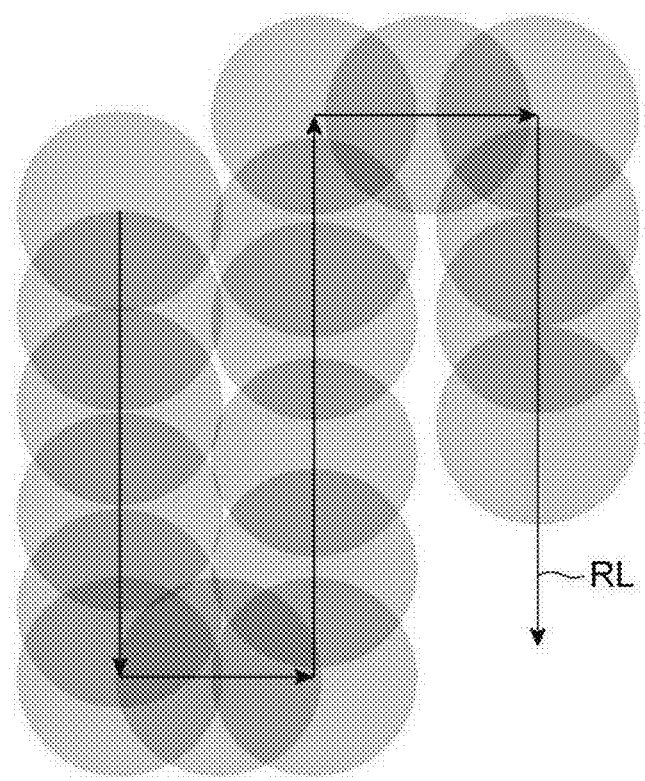
FIG. 10 is a conceptual diagram showing the dose distribution of the charged particle beam irradiated to each coordinate point.

The dose distribution calculation section 108 performs dose adjustment processing for calculating the dose of the charged particle beam R for each coordinate point in the layer L while performing adjustment in consideration of the passing distance of the charged particle beam R within the degrader 30 (step S250). As shown in FIG. 10, the dose of each coordinate point on the scanning path RL is calculated. A circle shown by the gray scale around each coordinate point indicates the dose distribution of the charged particle beam R at each coordinate point, and the dose increases as a color becomes dark. In addition, although the darkness of the gray scale of a circle at each coordinate point is fixed in FIG. 10 for the sake of simplicity, the darkness increases (dose increase) toward the center of the circle in practice.

Specifically, the dose distribution calculation section 108 calculates a passing distance of the charged particle beam R within the degrader 30 (step S260). As shown in FIG. 5, when the irradiation axis is deflected at the deflection angle θ with respect to the base axis AX, the passing distance of the charged particle beam R within the degrader 30 is "A/cos θ". Accordingly, when the charged particle beam R is irradiated to the coordinate point (x1, y1, θ1) in the N-th layer L, the passing distance of the charged particle beam R within the degrader 30 becomes longer by (A/cos θ1−A)=α than that when the charged particle beam R passes through the degrader 30 by the thickness A (A is the thickness of the degrader 30).

In addition, the dose distribution calculation section 108 corrects the range at each coordinate point on the basis of the passing distance calculated in step S260 (step S270). When the passing distance within the degrader 30 is longer by α, it can be calculated that the range of the charged particle beam R is shorter by kα than that when the charged particle beam R passes through the degrader 30 by the thickness A. In addition, k is a predetermined coefficient, and is determined in advance by test, simulation, or the like. In this case, when the amount of reduction in the range (=kα) is smaller than the half (β/2) of the distance β between layers, the range of the coordinate point (x1, y1) is not corrected. That is, the next operation is performed on the assumption that the charged particle beam R is irradiated to the coordinate point (x1, y1) of the N-th layer L that is the target of the operation. On the other hand, when the amount of reduction in the range (=kα) is equal to or greater than β/2, the range of the coordinate point (x1, y1) is corrected. Specifically, a setting condition before correction in which the charged particle beam R is irradiated to the coordinate point (x1, y1) of the N-th layer L is changed to a setting condition in which the charged particle beam R is irradiated to the coordinate point (x1, y1) of the (N+1)-th layer on the upstream side of the N-th layer L by correcting the range to the upstream side by β. In addition, when the amount of reduction in the range (=kα) becomes much larger, the range may be corrected by determining that the charged particle beam R is irradiated to the coordinate point (x1, y1) in the (N+2)-th layer, (N+3)-th layer, and the like. Therefore, not only the dose of the charged particle beam R irradiated to the coordinate point, at which the amount of reduction in the range (=kα) is smaller than β/2, but also the dose of the charged particle beam R irradiated to each coordinate point in other layers L ((N−1)-th layer L, (N−2)-th layer L, ...) on the downstream side, which belongs to the N-th layer L by correction, is added to the N-th layer L.

Figure 13B:
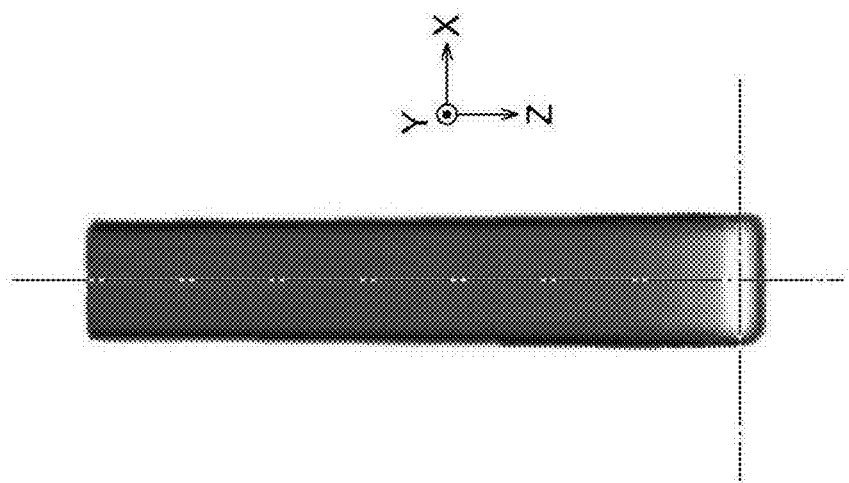
FIGS. 13A and 13B are images showing an example of the dose distribution of the charged particle beam.
Figure 13A:
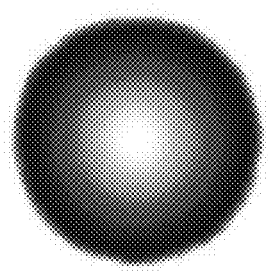

Then, the dose distribution calculation section 108 calculates a dose at each coordinate point in the N-th layer L on the basis of the range correction result in step S270 (step S280). As the dose distribution when irradiating the charged particle beam R to the coordinate point, data measured in advance is used. For example, as shown in FIGS. 13A and 13B, data obtained by irradiating the charged particle beam R into the water phantom and measuring the dose distribution in the water is used. In FIGS. 13A and 13B, a light-colored portion has a high dose, and a deep-colored portion has a low dose.

Figure 11:
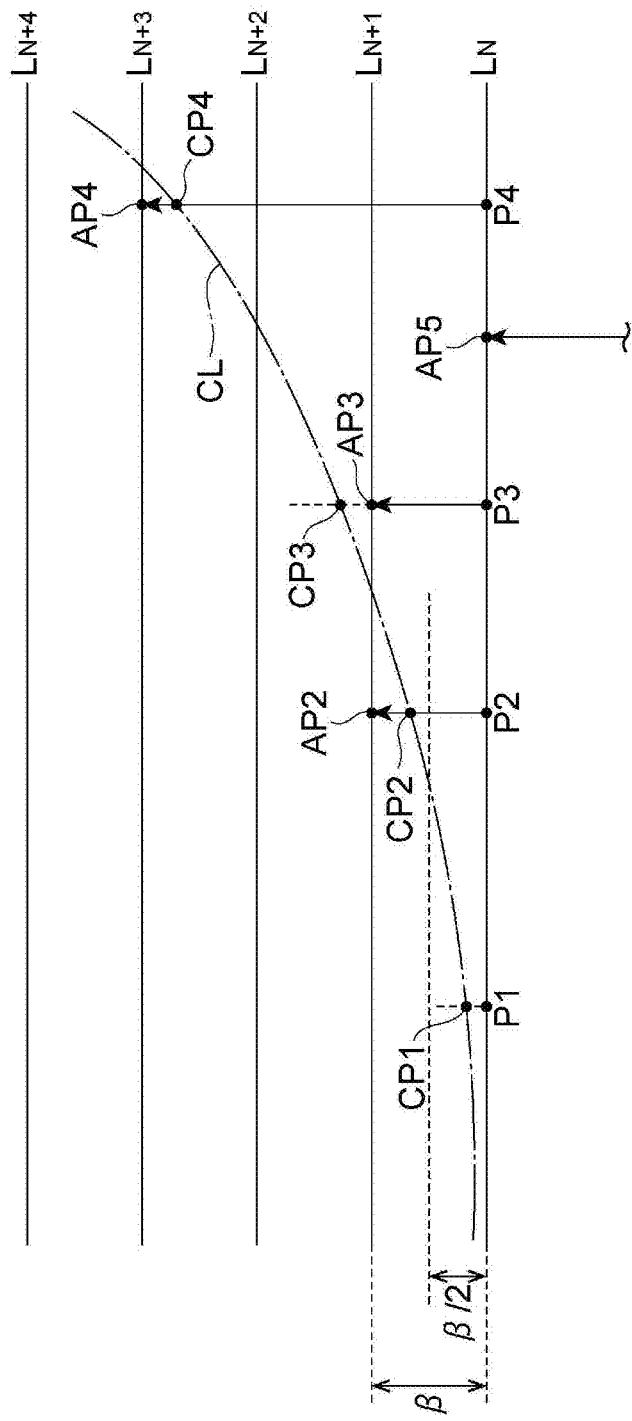
FIG. 11 is a conceptual diagram for explaining the dose adjustment processing.

A specific dose adjustment process will be described with reference to FIG. 11. First, in the process of S240, it is assumed that the coordinate points P1, P2, P3, and P4 are set in the N-th layer L (hereinafter, referred to as a layer LN) (in addition, these coordinate points are referred to as "setting coordinate points" for the sake of explanation). In addition, the graph CL shown by the one-dot chain line in FIG. 11 is obtained by calculating and plotting the amount of reduction in the range (=kα) for all coordinate points in the layer LN. This graph CL is shown only for illustrative purpose. In the actual treatment plan, creating the graph CL is not performed, and only the amount of reduction in the range (=kα) is calculated for each setting coordinate point P in order to reduce the load of the operation. In addition, it is also possible to create all or part of the graph CL.

Then, in the process of S260, the dose distribution calculation section 108 calculates a passing distance of the charged particle beam R within the degrader 30 for each of the setting coordinate points P1, P2, P3, and P4. Accordingly, the amount of reduction in the range (=kα) for each of the setting coordinate points P1, P2, P3, and P4 is calculated. Calculated coordinate points CP1, CP2, CP3, and CP4 obtained by subtracting the amount of reduction in the range (=kα) are shown in FIG. 11 for the sake of explanation. Then, in the process of S260, the dose distribution calculation section 108 corrects the range on the basis of the amount of reduction in the range (=kα) for each of the setting coordinate points P1, P2, P3, and P4.

First, the calculated coordinate point CP1 corresponding to the setting coordinate point P1 is present within the range of β/2 from the layer LN. Accordingly, correction is not made, and the calculated coordinate point CP1 still belongs to the layer LN. The calculated coordinate point CP2 corresponding to the setting coordinate point P2 is present on the more upstream side than the range of β/2 from the layer LN. Accordingly, correction is made, and the calculated coordinate point CP2 is added as a corrected coordinate point AP2 in a layer LN+1. The calculated coordinate point CP3 corresponding to the setting coordinate point P3 is present on the upstream side of the layer LN+1 but is present within the range of β/2 from the layer LN+1. Accordingly, correction is made, and the calculated coordinate point CP3 is added as a corrected coordinate point AP3 in the layer LN+1. The calculated coordinate point CP4 corresponding to the setting coordinate point P4 is present on the upstream side of a layer LN+2 and is present within the range of β/2 on the downstream side of a layer LN+3. Accordingly, correction is made, and the calculated coordinate point CP4 is added as a corrected coordinate point AP4 in the layer LN+3. In addition, a corrected coordinate point AP5 that has been added to the layer LN by correction in a layer on the downstream side of the layer LN belongs to the layer LN. As described above, since the setting coordinate point P1 and the corrected coordinate point AP5 belong to the layer LN, the dose of the charged particle beam R for the coordinate points P1 and AP5 is calculated. Accordingly, in addition to the dose of the charged particle beam R for the setting coordinate point P, the dose of the charged particle beam AP for the corrected coordinate point AP is added (for example, see FIG. 12). In addition, the corrected coordinate points AP2, AP3, and AP4 do not belong to the layer LN for which the dose is calculated, but the corrected coordinate points AP2, AP3, and AP4 are temporarily stored in the storage section 104 for later use in calculation in other layers.

Returning to FIG. 7, after the process of S280 ends, the control unit 101 determines whether or not N is Nmax (number of the layer L present on the most upstream side among the layers L) (step S290). When it is determined that N has not reached Nmax in S290, N is incremented (N=N+1) (step S300), and the process returns to step S230 to calculate a dose for the layer L on the immediate upstream side. On the other hand, when it is determined that N=Nmax is satisfied in step S290, it is regarded that dose calculation for all layers L has been completed, and the process shown in FIG. 7 ends, returning to the process of FIG. 6.

Figure 12:
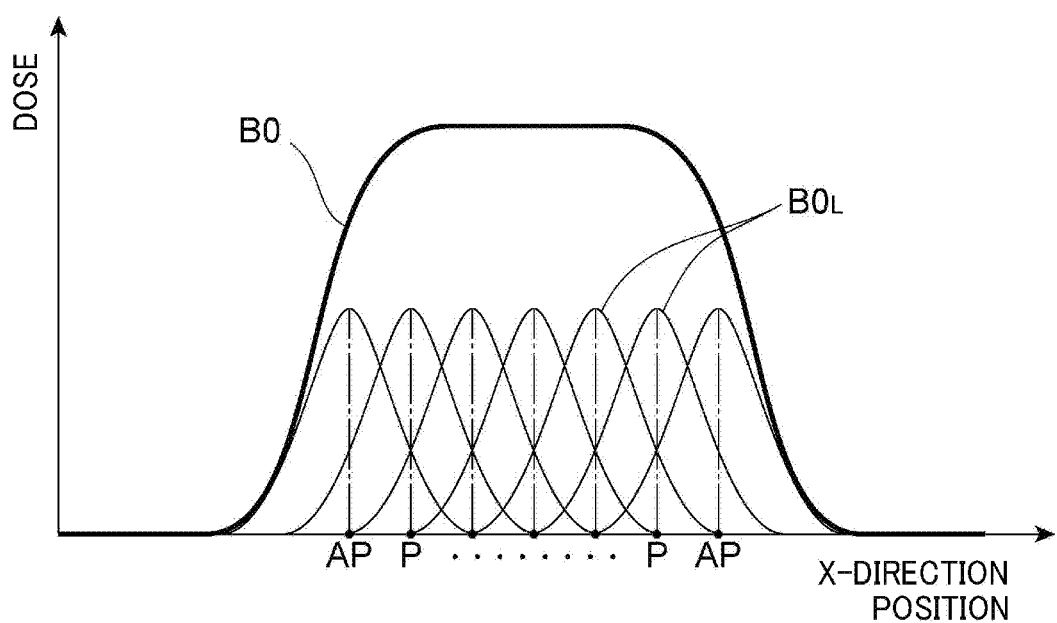
FIG. 12 is a graph showing the superposition of the doses at the coordinate points.
Figure 14:
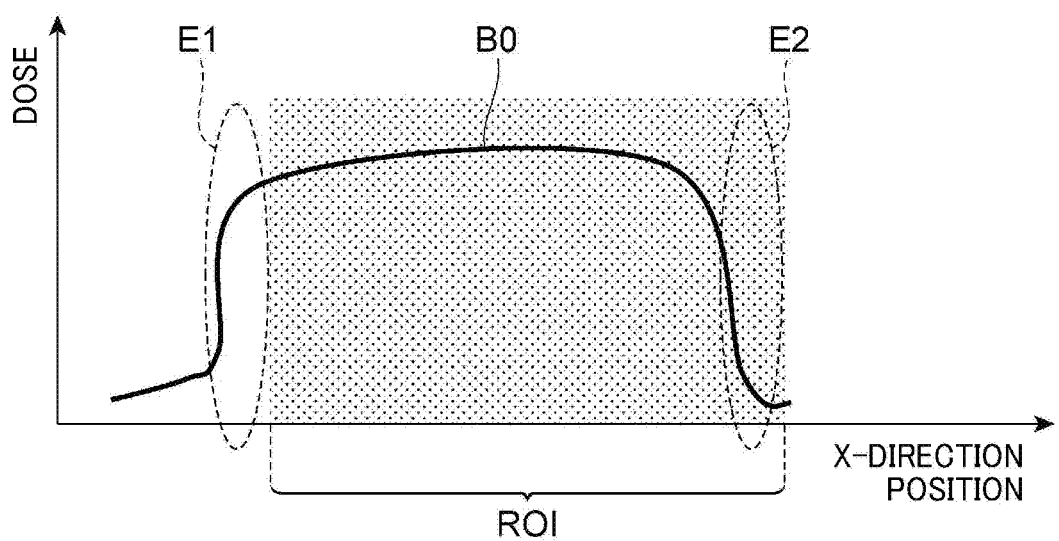
FIG. 14 is a graph for comparison of the dose distribution and the ROI.

As shown in FIG. 6, the dose distribution calculation section 108 calculates the dose distribution by superimposing the dose at each coordinate point on the basis of the operation result in step S200 (step S130). As shown in FIG. 12, the dose distribution calculation section 108 calculates the overall dose distribution B0 by superimposing the dose distribution B0L set for each coordinate point (setting coordinate point P and corrected coordinate point AP) of the layer L. Then, the dose distribution calculation section 108 performs determination of OK or NG by comparing the dose distribution B0 calculated in S130 with that in the ROI and evaluating the dose distribution B0 (step S140). For example, when a portion having a high dose is present in a region other than the ROI as a portion indicated by E1 in FIG. 14, determination as NG can be made. In addition, when a portion having a low dose is present in the ROI as a portion indicated by E2 in FIG. 14, determination as NG can be made. In addition, although the calculation and evaluation are performed in only one direction (X direction) of the scanning direction for understanding of explanation in FIGS. 12 and 14, the calculation and evaluation are also performed in the Y direction. In addition, the calculation and evaluation of the dose distribution are performed for all layers L. In addition, the dose distribution calculation section 108 may perform comparison and evaluation by performing an operation, or may perform evaluation on the basis of a user's input. When the evaluation is performed on the basis of a user's input, the dose distribution calculation section 108 outputs the dose distribution to the display unit 102. The user performs comparison and evaluation by referring to the dose distribution displayed on the display unit 102, and inputs OK or NG by operating the input unit 103. The dose distribution calculation section 108 performs determination of OK or NG by acquiring the user input information. When the determination is NG in step S140, the process returns to step S200 in which another scanning pattern is created and the dose distribution is calculated and evaluated.

When the determination is OK in step S140, the control pattern creation section 109 determines the scanning pattern, which has been determined to be OK in step S140, as a scanning pattern to be adopted for treatment (step S150). Then, the control pattern creation section 109 creates a control pattern of the scanning electromagnets 3a and 3b on the basis of the scanning pattern determined in step S150 (step S160). The control pattern creation section 109 creates the control pattern of the scanning electromagnets 3a and 3b so that the charged particle beam R is irradiated to the tumor 14 according to the created scanning pattern. When step S160 is completed, the process shown in FIG. 6 is ended and accordingly the creation of the treatment plan is ended.

Next, the operations and effects of the charged particle beam treatment planning device 100 according to the present embodiment will be described.

First, a charged particle beam treatment planning device in the related art will be described with reference to FIG. 5 for comparison. The degrader 130 has a plate shape (with a fixed thickness of A) extending in the X and Y directions, and an upstream side surface 30a and a downstream side surface 30b of the degrader 30 are planes perpendicular to the base axis AX. That is, cross-sections of the upstream side surface 30a and the downstream side surface 30b in the irradiation direction are rectangles. When the degrader 30 is used, the charged particle beam R1 whose irradiation axis matches the base axis AX is perpendicularly incident on the upstream side surface 30a of the degrader 30. Accordingly, the passing distance within the degrader 30 is A which is the same as the thickness of the degrader 30. On the other hand, the passing distance of the charged particle beam R2, of which the irradiation axis is deflected with respect to the base axis AX, within the degrader 30 is greater than A. Specifically, when the irradiation axis of the charged particle beam R2 is deflected at the deflection angle θ with respect to the base axis AX, the passing distance within the degrader 30 is "A/cos θ". Accordingly, the range of the charged particle beam R2 is shorter than that of the charged particle beam R1.

The charged particle beam treatment planning device in the related art has created a scanning pattern of the charged particle beam R for a predetermined layer LT without taking into consideration the above-described relationship between the passing distance of the charged particle beam R within the degrader 30 and the range, and the charged particle beam irradiation apparatus 1 has irradiated the charged particle beam R on the basis of the scanning pattern. Accordingly, the charged particle beam R1 whose irradiation axis matches the base axis AX is irradiated to the layer LT as planned, but the charged particle beam R2 whose irradiation axis is deflected with respect to the base axis AX is irradiated to a position on the upstream side of the layer LT. For this reason, since an actual dose of the charged particle beam R irradiated to the predetermined position of the tumor 14 is different from the dose calculated in the treatment planning, there is a problem in that the accuracy of a treatment plan lowers.

In contrast, the charged particle beam treatment planning device 100 according to the present embodiment includes the control unit 101 that adjusts the dose of the charged particle beam R, which is irradiated to the predetermined position of the tumor 14, on the basis of the passing distance of the charged particle beam R within the degrader 30 that is calculated using the deflection angle θ of the charged particle beam R. Therefore, even if the passing distance of the charged particle beam R within the degrader 30 changes with the deflection angle θ of the charged particle beam R, it is possible to suppress the occurrence of a difference between the treatment plan and the actual irradiation since the control unit 101 can adjust the dose in consideration of the passing distance. As a result, it is possible to create a high-accuracy treatment plan.

In addition, in the charged particle beam treatment planning device 100 according to the present embodiment, the dose distribution calculation section 108 of the control unit 101 calculates the dose distribution of the charged particle beam R irradiated to the tumor 14 by adding the dose of the charged particle beam R, which is irradiated to a predetermined irradiation position of the predetermined layer L, to the dose of the charged particle beam R irradiated to an irradiation position of another layer L, which is located on the more upstream side in the tumor 14 than the layer L in the irradiation direction of the charged particle beam R, on the basis of the passing distance of the charged particle beam R within the degrader 30. Therefore, even if the range becomes short due to an increase in the passing distance of the charged particle beam R within the degrader 30 and accordingly the charged particle beam R is irradiated to the more upstream side than the irradiation position of the predetermined layer L, the dose distribution calculation section 108 can calculate the dose distribution by adding the dose of the charged particle beam R irradiated to the irradiation position of the predetermined layer L to the dose of the charged particle beam R irradiated to the irradiation position of another layer L on the upstream side in consideration of such a dose of the charged particle beam. As a result, since it is possible to suppress the occurrence of a difference between the dose distribution calculated in the treatment planning and the actual dose distribution, it is possible to create a high-accuracy treatment plan.

In addition, in the charged particle beam treatment planning device 100 according to the present embodiment, when the amount of decrease in the range of the charged particle beam R due to the change of the passing distance of the charged particle beam R within the degrader 30 when irradiating the charged particle beam R to a predetermined irradiation position after deflecting the charged particle beam R in the predetermined layer L with respect to the passing distance of the charged particle beam R within the degrader 30 when irradiating the charged particle beam R without deflecting the charged particle beam R in the predetermined layer L is greater than β/2, the dose distribution calculation section 108 calculates the dose distribution of the charged particle beam R irradiated to the tumor 14 by adding the dose of the charged particle beam R, which is irradiated to the irradiation position of the predetermined layer L, to the dose of the charged particle beam R irradiated to the irradiation position of another layer L on the upstream side. The dose distribution calculation section 108 improves the accuracy by adding the dose of the charged particle beam R to the dose of the charged particle beam R irradiated to the irradiation position of another layer L on the upstream side when the amount of decrease in the range is large, while the dose distribution calculation section 108 determines that there is little influence and does not perform the addition when the amount of decrease in the range is small. In this manner, it is possible to reduce the load of the operation while improving the accuracy of a treatment plan.

The present invention is not limited to the above-described embodiment.

Although FIGS. 6 and 7 show an example of the process of treatment plan for the charged particle beam irradiation apparatus 1 using a scanning method, it is also possible to create a treatment plan for the charged particle beam irradiation apparatus 1 using a wobbler method. Also in this case, the control unit 101 may adjust the dose of the charged particle beam R, which is irradiated to the predetermined position of the tumor 14, on the basis of the passing distance of the charged particle beam R within the degrader 30.

Figure 15A:
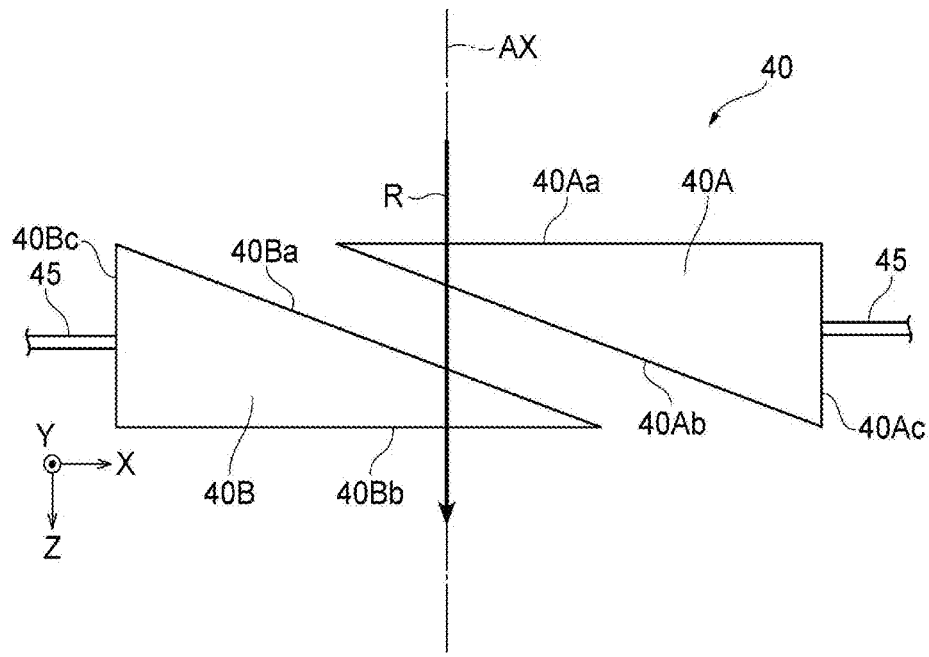
FIGS. 15A and 15B are schematic diagrams showing degraders in modifications.
Figure 15B:
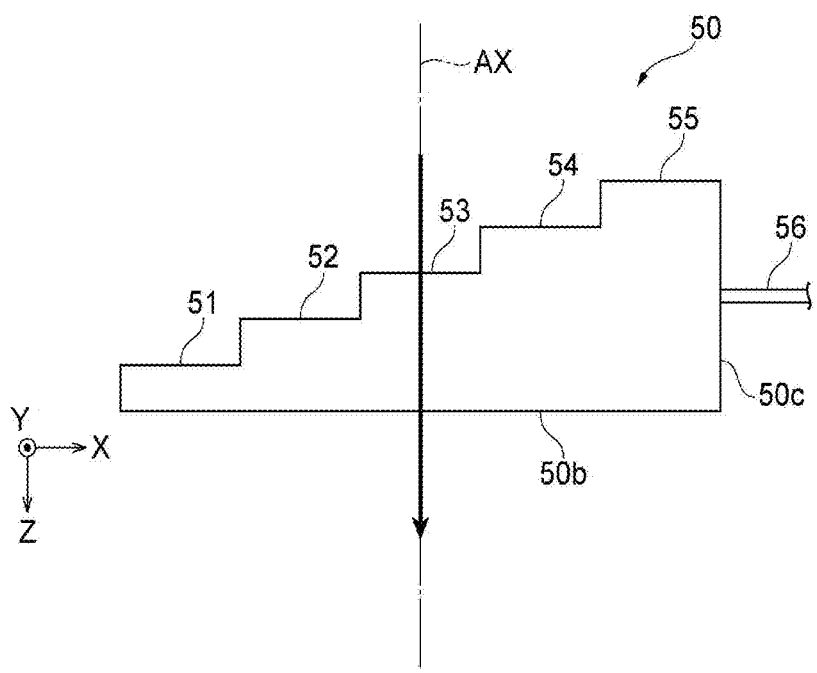

For example, although the example in which the plate-like degrader 30 is used has been described in the embodiment described above, it is also possible to use degraders 40 and 50 shown in FIGS. 15A and 15B.

As shown in FIG. 15A, certain embodiments of the present invention may be applied to a wedge-shaped degrader 40. In the degrader 40 shown in FIG. 15A, degraders 40A and 40B having right-angled triangular cross-sections are made to face each other in the Z direction, and each of the degraders 40A and 40B are moved in the X direction by an actuator 45 in order to adjust the range.

As shown in FIG. 15A, the degrader 40A disposed on the upstream side has an upstream side surface 40Aa corresponding to the long side (perpendicular to the base axis AX) of the cross-section of the right-angled triangle, a downstream side surface 40Ab corresponding to the hypotenuse, and a side surface 40Ac corresponding to the short side (parallel to the base axis AX). The actuator 45 for making the degrader 40A reciprocate in the X direction is connected to the side surface 40Ac. The degrader 40B disposed on the downstream side has an upstream side surface 40Ba corresponding to the hypotenuse of the cross-section of the right-angled triangle, a downstream side surface 40Bb corresponding to the long side (perpendicular to the base axis AX), and a side surface 40Bc corresponding to the short side (parallel to the base axis AX). The actuator 45 for making the degrader 40B reciprocate in the X direction is connected to the side surface 40Bc. The downstream side surface 40Ab of the degrader 40A and the upstream side surface 40Ba of the degrader 40B face each other so as to be parallel to each other. By moving the degraders 40A and 40B in the X direction using the actuator 45, it is possible to adjust the passing distance of the charged particle beam R passing through the inside of the degraders 40A and 40B (sum of the passing distance of the charged particle beam R passing through the inside of the degrader 40A and the passing distance of the charged particle beam R passing through the inside of the degrader 40B).

As shown in FIG. 15B, certain embodiments of the present invention may be applied to a stepwise degrader 50. The degrader 50 shown in FIG. 15B is formed in a stepped shape to have a plurality of portions with different thicknesses, and adjusts the range by changing the thickness of a portion on which the charged particle beam R is incident.

As shown in FIG. 15B, the degrader 50 has a configuration in which the thickness changes stepwise along the X direction. That is, the position of a downstream side surface 50b of the degrader 50 in the Z direction is constant in the entire region in the X direction, while upstream side surfaces 51, 52, 53, 54, and 55 are disposed in this order on the upstream side in the Z direction. When the degrader 50 is used, the range is adjusted by changing the upstream side surface on which the charged particle beam R is incident. An actuator 56 for making the degrader 50 reciprocate in the X direction is connected to the side surface 50c of the degrader 50.

It should be understood that the invention is not limited to the above-described embodiment, but may be modified into various forms on the basis of the spirit of the invention. Additionally, the modifications are included in the scope of the invention.

What is claimed is:

1. A charged particle beam treatment planning device that creates a treatment plan and is connected to a charged particle beam irradiation apparatus that includes a scanning electromagnet, which scans a charged particle beam, and a degrader, which adjusts a range of the charged particle beam by reducing energy of the charged particle beam, and irradiates an irradiation object with the charged particle beam, the device comprising:
   a control unit that adjusts a dose of the charged particle beam, which is irradiated to a predetermined position of the irradiation object, on the basis of a passing distance of the charged particle beam within the degrader calculated using a deflection angle of the charged particle beam.

2. The charged particle beam treatment planning device according to claim 1,
   wherein the control unit includes a dose distribution calculation section that calculates a dose distribution of the charged particle beam irradiated to the irradiation object, and
   the dose distribution calculation section calculates the dose distribution of the charged particle beam irradiated to the irradiation object by adding the dose of the charged particle beam irradiated to the predetermined position to a dose of the charged particle beam, which is irradiated to another position of the irradiation object on a more upstream side than the predetermined position in an irradiation direction of the charged particle beam, on the basis of the passing distance of the charged particle beam within the degrader.

3. The charged particle beam treatment planning device according to claim 2,
   wherein the control unit includes a layer setting section that virtually divides the irradiation object into a plurality of layers along the irradiation direction of the charged particle beam,
   the layer setting section sets a distance between the layers to β, and
   when an amount of decrease in the range of the charged particle beam due to a change of the passing distance when irradiating the charged particle beam to the predetermined position after deflecting the charged particle beam in one layer with respect to the passing distance when irradiating the charged particle beam without deflecting the charged particle beam in the one layer is greater than β/2, the dose distribution calculation section calculates the dose distribution of the charged particle beam irradiated to the irradiation object by adding the dose of the charged particle beam irradiated to the predetermined position to a dose of the charged particle beam irradiated to another position in another layer located on an upstream side of the one layer.

4. A charged particle beam treatment planning device that creates a treatment plan and is connected to a charged particle beam irradiation apparatus including an irradiation nozzle, in which a scanning electromagnet that scans a charged particle beam and a degrader that is provided on a downstream side of the scanning electromagnet and adjusts a range of the charged particle beam by reducing energy of the charged particle beam are housed, the device comprising:
   a storage unit that stores a CT image of the irradiation object;
   a layer setting section that virtually divides the irradiation object into a plurality of layers along an irradiation direction of the charged particle beam on the basis of the CT image stored in the storage unit;
   an irradiation position setting unit that sets an irradiation position of the charged particle beam in each of the plurality of layers; and
   a dose distribution calculation unit that, on the basis of a passing distance of the charged particle beam within the degrader when irradiating the charged particle beam to a predetermined irradiation position in a predetermined layer of the plurality of layers, calculates a dose distribution of the charged particle beam irradiated to the irradiation object by adding a dose of the charged particle beam irradiated to the predetermined irradiation position to a dose of the charged particle beam irradiated to an irradiation position in a layer located on a more upstream side in the irradiation object than the predetermined irradiation position in the irradiation direction of the charged particle beam.

5. A charged particle beam treatment planning method for creating a treatment plan for charged particle beam treatment, comprising:
   calculating a passing distance of a charged particle beam within a degrader, which adjusts a range of the charged particle beam, using a deflection angle of the charged particle beam; and
   adjusting a dose of the charged particle beam irradiated to a predetermined position of an irradiation object on the basis of the calculated passing distance.

6. The charged particle beam treatment planning method according to claim 5, further comprising:
   calculating a dose distribution of the charged particle beam irradiated to the irradiation object by adding the dose of the charged particle beam irradiated to the predetermined position to a dose of the charged particle beam, which is irradiated to another position of the irradiation object on a more upstream side than the predetermined position in an irradiation direction of the charged particle beam, on the basis of the calculated passing distance.

7. The charged particle beam treatment planning method according to claim 6, further comprising:
   virtually dividing the irradiation object into a plurality of layers along the irradiation direction of the charged particle beam every distance β; and
   when an amount of decrease in a range of the charged particle beam due to a change of the passing distance when irradiating the charged particle beam to the predetermined position after deflecting the charged particle beam in one layer with respect to the passing distance when irradiating the charged particle beam without deflecting the charged particle beam in the one layer is greater than β/2, calculating the dose distribution of the charged particle beam irradiated to the irradiation object by adding the dose of the charged particle beam irradiated to the predetermined position to a dose of the charged particle beam irradiated to another position in another layer located on an upstream side of the one layer.

* * * * *